Figure 1:
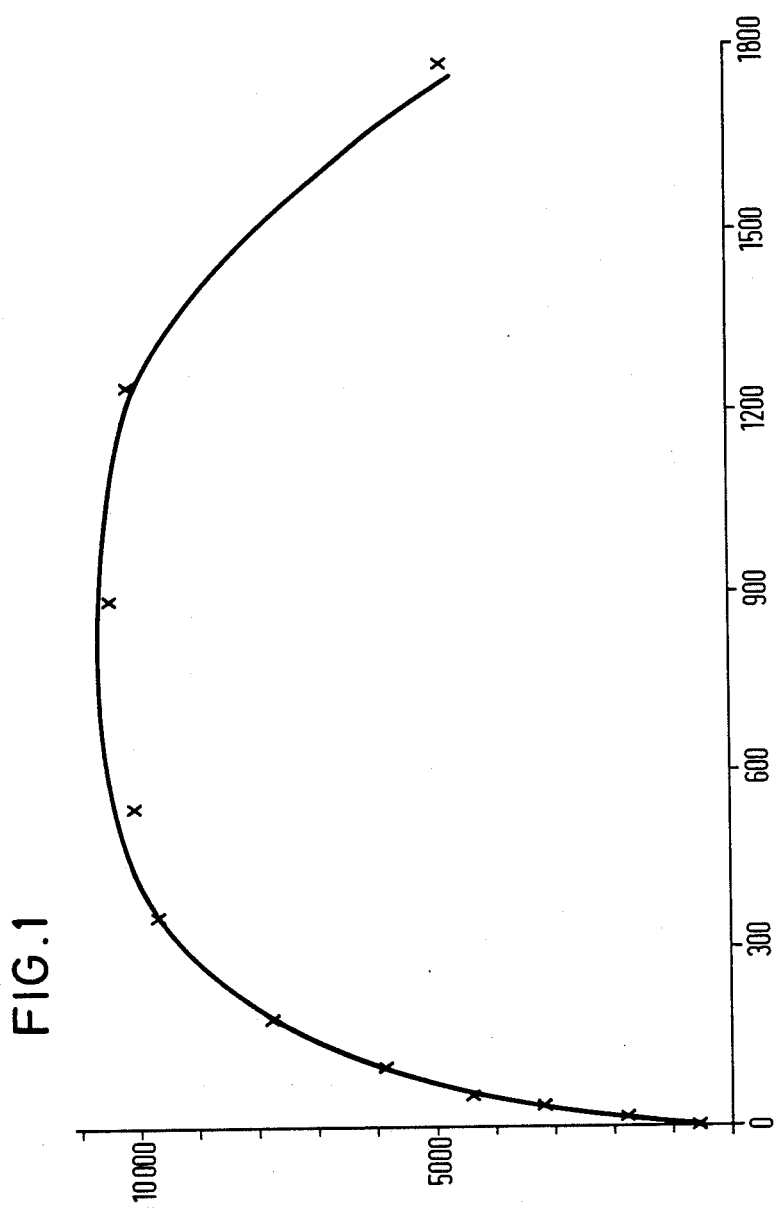

United States Patent [19]

Wulff et al.

[11] Patent Number: 4,834,918

[45] Date of Patent: May 30, 1989

[54] PROCESS AND REAGENT FOR INCREASING THE QUANTUM YIELD IN CHEMILUMINESCENT REACTIONS

[75] Inventors: Karl Wulff, Carmel, Ind.; Marin Berger, Weilheim-Unterhausen, Fed. Rep. of Germany

[73] Assignee: Boehringer Mannheim GmbH, Mannheim, Fed. Rep. of Germany

[21] Appl. No.: 939,867

[22] Filed: Dec. 10, 1986

[30] Foreign Application Priority Data

Dec. 20, 1985 [DE] Fed. Rep. of Germany ....... 3545398

[51] Int. Cl.$^4$ ............................................. C09K 11/00
[52] U.S. Cl. .................... 252/700; 436/513; 536/27
[58] Field of Search ........................ 252/700; 436/513; 536/27

[56] References Cited

U.S. PATENT DOCUMENTS

| | | | |
|---|---|---|---|
| 4,220,450 | 9/1980 | Maggio | 436/500 X |
| 4,277,437 | 7/1981 | Maggio | 436/513 X |
| 4,358,535 | 11/1982 | Falkow et al. | 436/504 X |
| 4,372,745 | 2/1983 | Mandle et al. | 436/537 |
| 4,478,817 | 10/1984 | Campbell et al. | 436/547 X |
| 4,709,016 | 11/1987 | Giese | 536/27 |

FOREIGN PATENT DOCUMENTS

| | | |
|---|---|---|
| 0087959 | 9/1983 | European Pat. Off. . |
| 0116454 | 8/1984 | European Pat. Off. . |
| 0157629 | 10/1985 | European Pat. Off. . |
| 58-158542 | 9/1983 | Japan . |
| 2162946 | 2/1986 | United Kingdom . |

OTHER PUBLICATIONS

Kalkar, et al., "Aqualuminescence . . . ", Appl. Radiat. Isot., vol. 37, No. 1, pp. 41–45, 1986 (CA104:158624).
Nikokavouras et al. "Chemiluminescence . . . " Chem. Chron. 1976, 5(3) 223–9 (CA87:4862).
Lasovskey, et al. "Micellar . . . ", Bioelectrochem. Bioenerg. 1986, 15(1) 95–102. (CA105:69401).
Japanese Abstract 58-158542 vol. 7 No. 282 (p. 243) Dec. 16, 1983.
37 Nature vol. 305 (1983) Sep., No. 5930, Chesham, Bucks, Great-Britain.
Chemical Abstracts vol. 87:4862, 1977, p. 396.
Chemical Abstracts vol. 105:69401, 1986, p. 582.
73-Spectroscopy vol. 104:158624, 1986, p. 631.

*Primary Examiner*—Matthew A. Thexton
*Assistant Examiner*—Catherine S. Kilby
*Attorney, Agent, or Firm*—Felfe & Lynch

[57] ABSTRACT

The present invention provides a process for increasing the quantum yield in the case of the oxidation of luminol or of a 7-dialkylaminonaphthalene-1,2-dicarboxylic acid hydrazide, each alkyl radical of which contains up to 3 carbon atoms, by a peroxide compound in the presence of peroxidase (POD), wherein the reaction is carried out in the presence of fluorescein, the concentration of the fluorescein being in a concentration range which gives a quantum yield which is greater than the sum of the quantum yields of the individual chemiluminescing materials.

The present invention also provides a reagent for the determination of POD, wherein it contains luminol or a 7-dialkylaminonaphthalene-1,2-dicarboxylic acid hydrazide, each alkyl radical of which contains up to 3 carbon atoms, fluorescein, a hydrogen peroxide provider, a buffer substance (pH 7.5 to 9) and optionally a sequestering agent.

13 Claims, 3 Drawing Sheets

PROCESS AND REAGENT FOR INCREASING THE QUANTUM YIELD IN CHEMILUMINESCENT REACTIONS

The present invention is concerned with a process for increasing the quantum yield of the chemiluminescence in the case of the oxidation of luminol or luminol derivatives by peroxide compounds in the presence of peroxidase (POD).

Chemiluminescence reactions are procedures in which a molecule capable of fluoroescence is brought by chemical energy into an excited electron state from which energy is then emitted as visible light. Bioluminescence reactions are enzymatically catalysed chemiluminescence reactions in which oxygen acts as electron acceptor. However, the quantum yields (ratio of chemiluminescence light quanta per reacted molecule) are only about 1% (cf. K.D. Gundermann, Angew. Chem. 77, 572–580/1965; Chemiker-Zeitung, 99 (6), 279–285/1975).

The reaction of luminol (3-aminophthalic acid hydrazide) or of luminol derivatives with peroxides catalysed by peroxidase (POD) is used as an indicator reaction in immunoassays, whereby either POD or luminol can serve as label. Peroxidase (POD; donor: $H_2O_2$-oxidoreductase, EC 1.11.1.7) characterises a group of enzymes which catalyse the oxidation of a large number of organic compounds.

The determination of POD is of particular importance in combination with preceding reactions in which hydrogen peroxide is formed, for example for blood sugar determinations, as well as in the case of enzyme-immunological determination processes which use POD as labelling enzyme. Other analysis methods in which the determination of POD is of importance include, for example, the determinations of galactose, hydrogen peroxide, catalase and oxidases.

It is known to measure POD by the decrease of the hydrogen peroxide or of the hydrogen donor, as well as by the formation of an oxidised compound. The latter method is of especial importance, the substrates used therefor including, for example, di-o-anisidine, guaiacol or ABTS (2,2'-azinodi-[3-ethylbenzthiazoline-(6)-sulphonic acid]).

These known methods have admittedly proved useful but there is a need for methods of higher sensitivity in order to shorten the POD determination time in the scope of enzyme-immune tests. POD plays a large part, for example, as a labelling enzyme in the case of the so-called "enzyme-immuno assays" according to the ELISA principle (enzyme-linked immuno-sorbent assay). With the numerous commercially available test reagents which depend upon this system, the period of time of the actual POD determination, for example with ABTS as substrate, is about 60 minutes, is extremely unsatisfactory.

For solving this problem, attempts have been made to make the reaction of luminol with peroxide compounds, catalysed by peroxidase, more sensitive by increasing the quantum yield.

Federal Republic of Germany Patent Specification No. 29 06 732 describes a process for the activity determination of peroxidases with the help of a chemiluminescence reaction which provides a good quantum yield and this makes possible, in the scope of enzyme-immuno-assays, an increase of the sensitivity of the POD determination and a substantial decrease of the period of time required for the determination.

The reaction of luminol with a peroxide compound forms the basis of the chemiluminescence reaction; however, instead of luminol, 7-dimethylaminonaphthalene-1,2-dicarboxylic acid hydrazide is used, an increase of the quantum yield of the chemiluminescence (chemiluminescence yield) thereby being achieved.

From Whitehead et al., Nature, 305, 158–159/1983, it is known to increase by a multiple the luminescence yield of the POD-catalysed oxidation of luminol by an addition of firefly luciferin; such an increase is also known by an addition of 6-hydroxybenzothiazoles (cf. Thorpe et al., Anal. Biochem. 145, 96–100/1985) or by an addition of phenol derivatives (cf. Thorpe et al., Clin. Chem., 31, 1335–1341/1985; European Patent Specification No. 0116454).

With these processes, an increase of the quantum yield is admittedly achieved; however, they have the disadvantage that the necessary additives (activators) are not easily obtainable and/or, because of their poor solubility in water, can only be used in admixture with organic solvents.

Therefore, it is an object of the present invention to provide a process for increasing the quantum yield in the case of the oxidation of luminol by peroxide compounds in the presence of POD which avoids the above-mentioned disadvantages and which can be used for a sensitive and rapid determination of POD in enzyme-immune-assays. This object is achieved by the process according to the present invention.

We have found that the quantum yield in the case of the oxidation of luminol by peroxide compounds in the presence of POD can be increased when the reaction is carried out in the presence of fluorescein, there being a concentration range of fluorescein in which a super-additive (synergistic) quantum yield is achieved which is greater than the sum of the quantum yields of the individual chemiluminescing materials.

Thus, the present invention provides a process for increasing the quantum yield in the case of the oxidation of luminol or of a 7-dialkylaminonaphthalene-1,2-dicarboxylic acid hydrazide, each alkyl radical of which contains up to 3 carbon atoms, by a peroxide compound in the presence of POD, wherein the reaction is carried out in the presence of fluorescein, the concentration of the fluorescein being in a concentration range which gives a quantum yield which is greater than the sum of the quantum yields of the individual chemiluminescing materials.

It is known that fluorescein also shows chemiluminescent phenomena under the action of hydrogen peroxide (cf. Nilsson and Kearns, J. Phys. Chem. 78, 1681–1683/1974); this is used in immuno-assays for the determination of compounds labelled with fluorescein (cf. European Patent Specifications Nos. 0054952 and EP-A-004653 and Federal Republic of Germany Patent Specification No. 31 32 491). From the work of B.A. Rusin et al. (Khim. Vys. Energ., 11 (1) 93–94/1977; referred to in CA 86, p.595, 130 321 s/1977), it is known that the chemiluminescence in the case of the oxidation of luminol is quenched by fluorescein. Therefore, it must be regarded as surprising that there is a concentration range in which a super-additive (synergistic) increase of the quantum yield of the chemiluminescent reaction occurs.

The alkyl groups in the 7-dialkylaminonaphthalene-1,2-dicarboxylic acid hydrazide can be different but are preferably the same and can be branched or preferably straight-chained and include, for example, methyl, ethyl, propyl and/or isopropyl.

7-Dimethylaminonaphthalene-1,2-dicarboxylic acid hydrazide is preferably used.

As peroxides, besides hydrogen peroxide, there can also be used all peroxide compounds with a comparable oxidation potential which are compatible with POD, for example alkali metal peroxides and addition compounds of hydrogen peroxide with boric acid (perborates) or with urea. There is preferably used, especially for enzyme immuno-assays, sodium perborate and, in particular, hydrogen peroxide.

The process according to the present invention is preferably carried out at a pH value of from 7.5 to 9 and especially at a pH value of about 8.5. As buffer, it is preferred to use potassium phosphate buffer or glycine-sodium hydroxide buffer although other conventional buffers, for example tris-HCl, tris-sulphate and tris-acetate, can also be used. The preferred buffer concentration is thereby from 10 to 1000 mmole/litre. The concentration of luminol or 7-dialkylaminonaphthalene-1,2-dicarboxylic acid hydrazide or of hydrogen peroxide lies, insofar as these concentrations are not to be determined with this reaction, in the concentration range usual for the chemiluminescence reaction; luminol or 7-dialkylaminonaphthalene-1,2-dicarboxylic acid hydrazide are preferably used in an amount of from 10 $\mu$mole/litre to 100 mmole/litre. The process according to the present invention is preferably carried out at the temperatures usual for enzymatic determinations which, as a rule, is from 20° to 37° C. but, for the process itself, lower or higher temperatures can also be used, an especially preferred temperature range being from 22° to 30° C.

The concentration range of fluorescein at which a super-additive (synergistic) increase of the quantum yield of the chemiluminescence reaction occurs can depend upon the nature and concentration of other reaction participants and the reaction conditions; however, for the particular conditions employed, the optimum range can easily be determined by a few orientating experiments. Preferably, especially as indicator reaction for enzyme immuno-assays, luminol and hydrogen peroxide is oxidised in the presence of POD; this reaction is preferably carried out in the presence of fluorescein, using a fluorescein concentration in the range of from 10 to 1000 $\mu$mole/litre and preferably of from 20 to 100 $\mu$mole/litre. In this range, an increase of the quantum yield is obtained which corresponds to about the tenfold of the yield which is given from the sum of the quantum yields of the particular individual chemiluminescing materials.

Because of the high quantum yield, the process according to the present invention can serve as indicator reaction (chemiluminescence test) for the determination of the POD activity in immuno-assays, in which, in comparison with a test with luminol as sole substrate, a tenfold increase of the sensitivity is achieved. Apart from the determination of POD, the process according to the present invention can, however, also be used for the determination of the peroxides participating in the reaction, for example of hydrogen peroxide, or for the determination of luminol or of a 7-dialkylaminonaphthalene-1,2-dicarboxylic acid hydrazide.

Thus, with the process according to the present invention, it is, for example, possible to reduce the measurement time for the pure enzyme activity determination in the case of the ELISA tests, with a high sensitivity, to about 2 to 3 minutes. The measurement preferably takes place in such a manner that the amount of light emitted in a definite time interval is measured.

Therefore, the present invention is also concerned with the use of the process according to the present invention for the determination of POD or of luminol or of a 7-dialkylaminonaphthalene-1,2-dicarboxylic acid hydrazide which serve especially as labelling substances in immuno-assays.

The POD determination with the use of the process according to the present invention can be carried out, for example, in the scope of an immunological hapten determination in which a known amount of a hapten labelled with POD is added to the sample to be investigated containing an unknown amount of the hapten, the sample is then contacted with a specific antibody of the hapten bound to a solid carrier, the solid is separated from the liquid phase and the POD activity is measured in one of the two phases (ELISA test). With this test, there can be determined, for example, digoxin, thyroxin ($T_4$) or insulin in blood serum, in which it is possible to work, for example, according to one of the methods described in Federal Republic of Germany Patent Specification No. 29 06 732.

The present invention also provides a reagent for the determination of POD according to the process of the present invention, wherein it contains luminol or a 7-dialkylaminonaphthalene-1,2-dicarboxylic acid hydrazide, each alkyl radical of which contains up to 3 carbon atoms, fluorescein, a hydrogen peroxide provider, a buffer substance (pH 7.5 to 9) and optionally a sequestering agent.

A preferred reagent for one litre of test solution contains:
- 10 to 1000 $\mu$mole 7-dialkylaminonaphthalene-1,2-dicarboxylic acid hydrazide or preferably luminol,
- 10 to 1000 $\mu$mole fluorescein,
- 50 to 500 mmole potassium phosphate or glycine buffer (pH 7.5 to 9),
- 10 to 200 $\mu$mole hydrogen peroxide and optionally 0.01 to 1 mmole of a sequestering agent.

As sequestering agents possibly to be used, there can be used substances known for this purpose, such as ethylenediamine-tetraacetic acid (EDTA) and the like. Furthermore, the reagent can contain conventional stabilising agents, such as serum albumin, carbohydrates and the like. As hydrogen peroxide provider, there can be used hydrogen peroxide itself, as well as known hydrogen peroxide-liberating substances, for example urea perhydrate ("solid $H_2O_2$") and the like.

Apart from the above-mentioned components, the reagent according to the present invention can also contain hapten labelled with POD, as well as a carrier-bound specific antibody against the particular hapten if the reagent is to be used in the scope of an enzyme immune test. In addition, there can be present other components which are conventional, for example, in such ELISA reagents, such as further buffer substances, stabilising agents and the like.

The following Examples are given for the purpose of illustrating the present invention; if nothing otherwise is stated, the percentages and amounts are by weight:

EXAMPLE 1.

This Example illustrates the influence of the fluorescein concentration on the quantum yield.

All experiments were carried out in a bioluminescence measurement apparatus of the firm Berthold, Wildbad, of the type Biolumat LB 9500. The test volume used was 500 μl. and the temperature 30° C.

The following concentrations (end concentrations in the test) were used:

| | |
|---|---|
| hydrogen peroxide | 0.1 mmole/l. |
| luminol | 25 μmole/l. |
| peroxidase | 20 mg./l. |
| tris-HCl buffer (pH = 8.5) | 90 mmole/l. |

FIG. 1 of the accompanying drawings illustrates graphically the dependence of the light emission on the fluorescein concentration. As FIG. 1 shows, the light emission at a fluorescein concentration of from 10 to 1000 μmole/l. is activated by a multiple.

EXAMPLE 2.

This example illustrates the super-additive (synergistic) effect in the case of the working together of luminol and fluorescein in comparison with a sole use of luminol or of fluorescein.

Working was with the following concentrations (end concentrations in the test):

| | |
|---|---|
| luminol | 0.1 mmole/l. |
| fluorescein | 25 μmole/l. |
| POD | 20 ng./l. |
| hydrogen peroxide | 0.1 mmole/l. |
| tris-HCl buffer (pH = 8.5) | 90 mmole/l. |

The following Table 1 summarises the results obtained, $I_{max}$ signifying the number of light emissions/2 seconds.

TABLE 1

| No. | POD | luminol | $H_2O_2$ | fluorescein | $I_{max}$(imp./2 sec.) |
|---|---|---|---|---|---|
| 1 | + | + | + | + | $3.9 \times 10^5$ |
| 2 | + | − | + | + | $5.8 \times 10^3$ |
| 3 | + | + | − | + | $8.4 \times 10^4$ |
| 4 | + | + | + | − | $2.7 \times 10^4$ |
| 5 | + | − | − | + | $7.2 \times 10^3$ |
| 6 | + | + | − | − | 432 |
| 7 | − | + | + | + | 25 |

From Table 1, the synergistic effect in the case of the working together of luminol and fluorescein can clearly be recognised. In the case of the presence of luminol and fluorescein, the maximum light intensity ($I_{max}$) is about ten times as great as the sum of the intensities of the reactions in the presence of luminol or of fluorescein alone (tests 2 and 4). Furthermore, it can be seen from Table 1 that fluorescein in the presence of POD also already reacts with atmospheric oxygen with chemiluminescence (cf. test 5).

EXAMPLE 3.

This Example shows the influence of the POD concentration on the reaction.

The measurement took place as in the preceding Examples, the following concentrations (end concentrations in the test) being used:

| | |
|---|---|
| luminol | 0.1 mmole/l. |
| hydrogen peroxide | 0.1 mmole/l. |
| fluorescein | 25 μmole/l. |
| tris-HCl buffer (pH = 8.5) | 90 mmole/l. |

There were obtained the results summarised in the following Table 2:

TABLE 2

| $C_{POD}$ (mol./l · $10^{-10}$) | $I_{max}$ (imp./2 sec.) with fluorescein | $I_{max}$ (imp./2 sec.) without fluorescein |
|---|---|---|
| 0 | 40 | 10 |
| 0.25 | 79 | 170 |
| 1.3 | 1580 | 1220 |
| 2.5 | 32500 | 670 |
| 3.1 | 45200 | 540 |
| 6.3 | 433600 | 3580 |
| 8.3 | 514900 | 4790 |
| 13 | greater than $10^6$ | 76000 |
| 17 | " | 93200 |
| 25 | " | 339200 |
| 130 | " | greater than $10^6$ |

EXAMPLE 4.

This Example shows the influence of the pH value on the reaction, using the concentrations given in Example 3. The POD concentration was $9 \times 10^{-10}$ mole/litre and the concentration of Tris-HCl buffer with various pH values was 90 mmole/litre. The pH values of 12.6 were achieved by the addition of 1 mole/litre aqueous sodium hydroxide solution.

Figure 2:
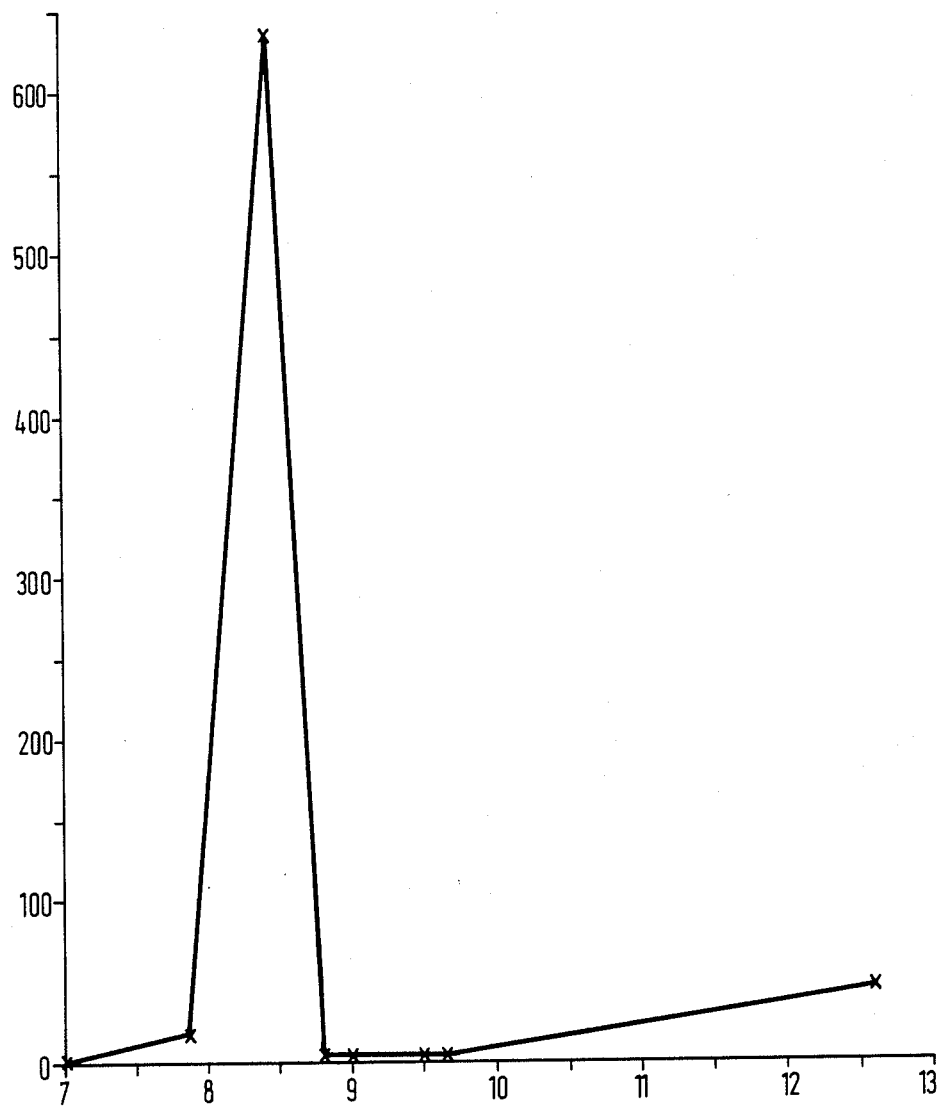

FIG. 2 of the accompanying drawings graphically illustrates the influence of the pH value on the light emission ($I_{max}$).

EXAMPLE 5.

Working was as in Example 2 but, instead of hydrogen peroxide, sodium perborate was used as the oxidation agent.

The following Table 3 summarises the results thereby obtained:

TABLE 3

| No. | POD | perborate | luminol | fluorescein | $I_{max}$ (imp./2 sec.) |
|---|---|---|---|---|---|
| 1 | + | + | + | + | $1.5 \cdot 10^5$ |
| 2 | + | + | − | + | 400 |
| 3 | + | + | + | − | $1.8 \cdot 10^4$ |
| 4 | + | − | − | + | $3.3 \cdot 10^3$ |

From the results given in Table 3, the super-additive effect in the case of working in the presence of luminol and fluorescein can also clearly by seen.

EXAMPLE 6.

This Example illustrates the use of the process according to the present invention in an enzyme immuneassay according to the ELISA principle for the determination of salivary α-amylase.

The test was carried out in the following way:

1. Luminescence test tubes (Lumacuvette P polystyrene, recorder No. 4960 of Lumac Systems AG, Basel, Switzerland) were incubated with a monoclonal antibody (5 μg./ml.) specifically binding the human salivary analysis against human salivary α-amylase in 50 mM carbonate buffer (pH=9.3) (500 μl.) for 18 hours at 4° C. This monoclonal antibody is deposited under the designation NCACC 84111305 with the National Collection of Animal Cell Cultures, Porton Down, England, and is produced according to European Patent Specification No. 0150309.

2. The test tubes were washed once with 150 mM phosphate buffer (pH=7.2, 145 mM NaCl) and 1% bovine serum albumin (BSA).

3. There followed an after-treatment of the test tubes (after-coating) with 150 mmole/litre phosphate buffer (pH 7.2), 145 mmole/litre sodium chloride and 2% bovine serum albumin. The test tubes were then left for 1 hour at ambient temperature.

4. The test tubes were washed as described under 2.

5. Human salivary α-amylase-POD conjugate was incubated at various concentrations for 4 hours at 37° C. in the luminescent test tubes (500 μl.).

6. Washing was carried out five times as described under 2.

7. (a) For the development, 1 ml. ABTS reagent (from Enzymun-Teste Digoxin, Boehringer Mannheim GmbH, catalogue order No. 199656) was introduced into each test tube. After precisely 9 minutes, the extinction was determined at 405 nm against non-incubated ABTS reagent.

(b) 500 μl. luminescence reagent without fluorescein were introduced into each test tube (end concentration see Example 2). After precisely 30 seconds or 17 minutes, the luminescence was measured (apparatus: bioluminescence measurement apparatus of the firm Berthold, Wildbad, of the type Biolumat LB 9500 T; integration time 60 sec.).

(c) 500 μl. luminescence solution with fluorescein (end concentration see Example 2) were added and then the luminescence was measured as described under 7.b).

Figure 3:
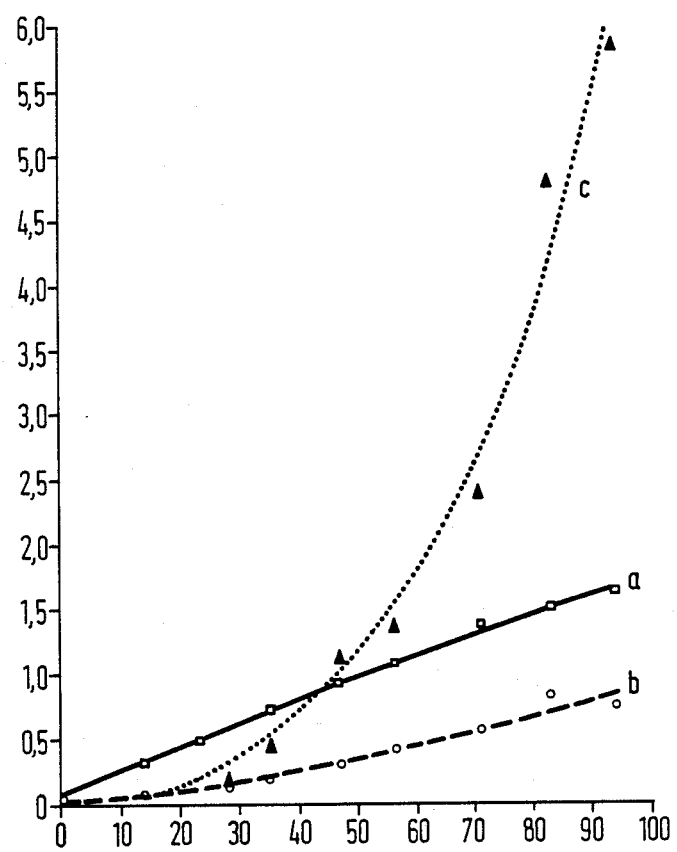

FIG. 3 of the accompanying drawings shows the calibration curves obtained with the indicator reaction (a), (b) and (c). The measurement signal obtained (in case a: light absorption; in cases b and c: light emission) is hereby illustrated as a function of the concentration of the bound salivary amylase-POD conjugate.

EXAMPLE 7.

Synergistic effect in the case of the use of 7-dimethylaminonaphthalene-1,2-dicarboxylic acid hydrazide (DNH).

Working was analogous to that described in Example 1. The end concentrations in the test were:

| | |
|---|---|
| DNH | 0.1 mmole/l. |
| fluorescein | 25 μmole/l. |
| POD | 20 ng./l. |
| hydrogen peroxide | 0.1 mmole/l. |
| tris-HCl buffer (pH 8.5) | 90.0 mmole/l. |

The following Table 4 summarises the results obtained:

TABLE 4

| No. | POD | DNH | $H_2O_2$ | fluorescein | $I_{max}$ (imp./2 sec.) |
|---|---|---|---|---|---|
| 1 | + | + | + | − | $1.1 \cdot 10^4$ |
| 2 | + | + | + | + | $6 \cdot 10^4$ |
| 3 | + | − | + | + | $4.0 \cdot 10^2$ |

From Table 4, it can be seen that in the case of the use of 7-dimethylaminonaphthalene-1,2-dicarboxylic acid hydrazide and fluorescein, a synergistic effect can be ascertained.

We claim:

1. A process for increasing the quantum yield resulting from an oxidation of luminol or of a 7-dialkylaminonaphthalene-1,2-dicarboxylic acid hydrazide each alkyl radical of which contains up to 3 carbon atoms, by a peroxide compound in the presence of peroxidase (POD), comprising carrying out the oxidation reaction in the presence of fluorescein, the concentration of the fluorescein being in a concentration range which gives a quantum yield which is greater than the sum of the quantum yields of the individual chemiluminescing materials.

2. The process of claim 1, wherein the peroxide compound is hydrogen peroxide.

3. The process of claim 1, wherein the reaction is carried out at a pH value of from 7.5 to 9.

4. The process of claim 3, wherein the reaction is carried out at a pH value of 8.5.

5. The process of claim 1, wherein luminol is oxidized with hydrogen peroxide in the presence of POD.

6. The process of claim 1 wherein the reaction is carried out in the presence of 10 to 1000 mole/litre fluorescein.

7. The process of claim 1 wherein the reaction is carried out at a pH of 7.5 to 9 in the presence of 10 to 1000 mole/litre fluorescein.

8. The process of claim 7 wherein luminol is oxidized with hydrogen peroxide in the presence of POD.

9. The process of claim 7 wherein the alkyl radicals are methyl, ethyl, propyl or isopropyl.

10. The process of claim 7 wherein the peroxide compound is hydrogen peroxide or sodium perborate.

11. In a reagent for the determination of POD by chemiluminescent measurements, of the type comprising a chemiluminescing agent selected from the group consisting of luminol and a 7-dialkylaminonaphtalene-1,2-dicarboxylic acid hydrazide, each alkyl radical of which contains up to 3 carbon atoms, a hydrogen peroxide provider, a buffer substance (pH 7.5 to 9) and optionally a sequestering agent the improvement comprising an amount of an additional chemiluminescing agent fluorescein which gives a quantum yield greater than the sum of quantum yields of the individual chemiluminescing materials.

12. The reagent of claim 11 wherein 10 to 1000 μmole/l fluorescein is present.

13. The reagent of claim 11, comprising:
   10 to 1000 μmole/l. luminol or 7-dialkylamino naphthalene-1,2-dicarboxylic acid hydrazide,
   10 to 1000 μmole/l. fluorescein,
   50 to 500 mmole/l. potassium phosphate or glycine buffer,
   10 to 200 μmole/l. hydrogen peroxide, and optionally
   0.01 to 1 mmole/l. of a sequestering agent.

* * * * *

UNITED STATES PATENT AND TRADEMARK OFFICE
CERTIFICATE OF CORRECTION

PATENT NO. : 4,834,918

DATED : May 30, 1989

INVENTOR(S) : Karl Wulfe, et al.

It is certified that error appears in the above-identified patent and that said Letters Patent is hereby corrected as shown below:

Col. 8, line 45
   new Claim 11:     delete "dialkylaminonaphtalene" and insert -- dialkylamino-naphthalene --.

Signed and Sealed this

Twenty-sixth Day of June, 1990

Attest:

HARRY F. MANBECK, JR.

Attesting Officer     Commissioner of Patents and Trademarks